(12) United States Patent
Chen et al.

(10) Patent No.: US 6,905,743 B1
(45) Date of Patent: *Jun. 14, 2005

(54) DIMENSIONALLY STABLE BALLOONS

(75) Inventors: John Jianhua Chen, Plymouth, MN (US); Lixiao Wang, Long Lake, MN (US); Yiqun Wang, Maple Grove, MN (US); Albert C. C. Chin, Newton, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 490 days.

This patent is subject to a terminal disclaimer.

(21) Appl. No.: 09/696,378

(22) Filed: Oct. 25, 2000

Related U.S. Application Data

(63) Continuation-in-part of application No. 09/426,384, filed on Oct. 25, 1999, now abandoned, which is a continuation-in-part of application No. 09/257,677, filed on Feb. 25, 1999, now Pat. No. 6,284,333.

(51) Int. Cl.[7] .......................................... A61M 25/10
(52) U.S. Cl. .............. 428/35.7; 604/96.01; 604/103.09; 604/103.11; 264/108; 264/172.13; 264/209.5; 525/314
(58) Field of Search ................. 428/35.7; 604/96.01, 604/103.09, 103.11; 264/108, 172.13, 209.5, 173.15; 525/314

(56) References Cited

U.S. PATENT DOCUMENTS

| | | | |
|---|---|---|---|
| 3,825,036 A | | 7/1974 | Stent .......................... 138/174 |
| 4,254,774 A | * | 3/1981 | Boretos ....................... 604/271 |
| 4,448,195 A | * | 5/1984 | LeVeen et al. .............. 128/344 |

(Continued)

FOREIGN PATENT DOCUMENTS

| | | |
|---|---|---|
| EP | 0 448 886 A1 | 12/1990 |
| EP | 0 420 488 B1 | 4/1991 |
| EP | 0 934 755 A2 | 8/1999 |
| EP | 1 008 363 A2 | 6/2000 |
| WO | 96/00752 | 1/1996 |
| WO | 97/24403 | 7/1997 |
| WO | 99/12586 | 3/1999 |
| WO | 00/50105 | 8/2000 |

OTHER PUBLICATIONS

Rau et al., WO 95/18647, Jul. 13, 1995.*
Mark Alger, Polymer Science Dictionary, $2^{nd}$ Edition, 1997.*
Yong Yang, Hydroxypropylcellulose, Polymer Data Handbook, Oxford University Press, Copyright 1999.*
Polymers—A Property Database Copyright CRC Press, LLC, 2000.*
U.S. Appl. No. 09/257,677, filed Feb. 25, 1999, Wang et al.
U.S. Appl. No. 09/426,384, filed Oct. 25, 1999, Chen et al.

*Primary Examiner*—Harold Pyon
*Assistant Examiner*—Sow-Fun Hon
(74) *Attorney, Agent, or Firm*—Vidas, Arrett and Steinkraus

(57) ABSTRACT

A medical balloon composed of a micro-composite material which provides for radial expansion of a balloon to a predetermined extent, but which has minimal longitudinal growing during balloon inflation. The micro-composite material includes a fibril component, a matrix component, and optionally, a compatibilizer. The fibril component may preferably be liquid crystal polymer fibers randomly scattered through out the balloon material. The liquid crystal polymers are created by extrusion at high speed. An alternative fibril component may be a PET fibers which are uniformly spaced about the balloon material and extend through out the length of the balloon material tube.

19 Claims, 3 Drawing Sheets

U.S. PATENT DOCUMENTS

| | | | |
|---|---|---|---|
| 5,156,785 A | 10/1992 | Zdrahala | 264/108 |
| 5,254,089 A | 10/1993 | Wang | 604/96 |
| 5,270,086 A | 12/1993 | Hamlin | 428/35.2 |
| 5,389,314 A | 2/1995 | Wang | 264/25 |
| 5,456,674 A | 10/1995 | Bos et al. | 604/280 |
| 5,458,572 A | 10/1995 | Campbell et al. | 604/96 |
| 5,512,051 A | 4/1996 | Wang et al. | 604/96 |
| 5,556,383 A | 9/1996 | Wang et al. | 604/96 |
| 5,647,848 A | 7/1997 | Jorgensen | 604/96 |
| 5,702,418 A | 12/1997 | Ravenscroft | 606/198 |
| 5,704,913 A | 1/1998 | Abele et al. | 604/101 |
| 5,755,690 A | 5/1998 | Saab | 604/96 |
| 5,797,877 A | 8/1998 | Hamilton et al. | |
| 5,807,327 A | 9/1998 | Green et al. | 604/96 |
| 5,830,182 A | 11/1998 | Wang et al. | 604/96 |
| 5,976,120 A | 11/1999 | Chow et al. | 604/525 |
| 6,059,751 A | 5/2000 | Ostapchenko et al. | 604/96 |
| 6,156,842 A * | 12/2000 | Hoenig et al. | 525/171 |
| 6,242,063 B1 * | 6/2001 | Ferrera et al. | 428/35.2 |
| 6,284,333 B1 * | 9/2001 | Wang et al. | 428/35.5 |
| 6,325,780 B1 * | 12/2001 | Schaible et al. | 604/103.06 |
| 6,443,925 B1 * | 9/2002 | Schaible et al. | 604/96.01 |

* cited by examiner

DIMENSIONALLY STABLE BALLOONS

CROSS-REFERENCE TO RELATED APPLICATIONS

This application is a continuation-in-part of U.S. patent application Ser. No. 09/426,384 filed Oct. 25, 1999 now abandoned which is a continuation-in-part of U.S. patent application Ser. No. 09/257,677 filed Feb. 25, 1999, now issued as U.S. Pat. No. 6,284,333.

BACKGROUND OF THE INVENTION

Medical catheters having a balloon mounted thereon are useful in a variety of medical procedures. A balloon may be used to widen a vessel into which the catheter is inserted by dilating the blocked vessel, such as in an angioplasty procedure. More significant to the present invention however, is the use of a catheter to deliver a medical device, such as a stent, into a body lumen. Some examples of stent delivery balloons are disclosed in U.S. Pat. No. 5,702,418, and U.S. Pat. No. 5,797,877, the entire contents of both patents is hereby incorporated by reference. In these and other medical device delivery applications, radial expansion of a balloon may be used to expand or inflate a stent at a desired positioned within the body. Using a balloon equipped catheter to deliver a stent requires precise positioning of the balloon and stent as well as a balloon with accurate and predictable expansion properties. A known drawback of many previous delivery catheters and balloons is that when a balloon is radially inflated to a desired extent, the balloon will also expand longitudinally. As a result of longitudinal expansion of a balloon during the delivery of a medical device, the balloon itself, the medical device mounted thereupon or both apparatuses may be shifted from their pre-inflation position resulting in improper delivery of the medical device.

In balloons where longitudinal expansion occurs, the balloon may expand longitudinally past one or both of the stent ends. Typical stent delivery balloons will expand longitudinally at least 5% beyond the original pre-inflation state. In addition to potentially mis-delivering the medical device as described above, the resulting extended balloon may cause the edges of the stent to push against the vessel wall to a greater extent than they would from radial expansion alone. The protruding stent edges may damage or tear the surrounding vessel resulting in potentially serious trauma for the patient.

It has recently been discovered that Liquid Crystal Polymers (LCP) may be effectively blended with other materials and extruded to form high strength medical balloons. In copending U.S. applications Ser. No. 08/926,905 (corresponding to PCT/US98/18345 filed Sept. 4, 1998), now issued as U.S. Pat. No. 6,242,063, and Ser. No. 09/257,677 filed Feb. 25, 1999, now issued as U.S. Pat. No. 6,284,333, there are described medical balloons made from LCP blends. The entire contents of both of these applications is hereby incorporated by reference.

U.S. Pat. No. 5,389,314 to Wang discloses an inflatable medical device which has a plurality of longitudinally oriented conduits which extend through out the length of the device. The device may be formed by co-extruding two dissimilar plastic materials. The first material form defining a discrete phase which forms fibers and the other material or continuous phase which forms the remaining balloon material. After extrusion the discrete phase is withdrawn from the continuous phase, leaving the continuous phase with a plurality of conduits therethrough.

BRIEF SUMMARY OF THE INVENTION

The present invention is directed generally to medical balloons which expand only to a predetermined extent, and which have minimal longitudinal and/or minimal radial growth during expansion. Specifically, the invention is directed to a stent delivery balloon composed of a micro-composite material which includes a longitudinal fibril structure that is either parallel to the longitudinal axis of the balloon structure, or that is diagonal to the longitudinal axis at the molecular level of the balloon. The orientation of the fibril structure can limit longitudinal expansion of the balloon and allow the balloon to expand radially as desired, but minimally, or not at all in the longitudinal direction if the fibrils are parallel to the balloon axis, or when the fibrils are oriented diagonally about the axis, can limit both longitudinal and radial expansion of the balloon when inflated.

The micro-composite material is made up of a combination of a fibril component, a semi-compliant balloon material which acts as a matrix, and optionally a compatibilizer material which may act to create a less distinctive phase boundary between the fibril and matrix components, but which does not solubilize the LCP polymer in the matrix at human body temperature.

The present invention provides for a balloon which utilizes LCP materials or other oriented materials such as PET, in combination with a thermoplastic elastomer matrix and an optional compatibilizer to form a micro-composite material. The present micro-composite material is suitable for construction balloons which exhibit minimal or no longitudinal growth during balloon expansion but which expands as desired in the radial direction, or the present micro-composite material is suitable for construction of balloons that exhibit minimal expansion both in the longitudinal and radial directions.

BRIEF DESCRIPTION OF THE SEVERAL VIEWS OF THE DRAWINGS

A detailed description of the invention is hereinafter described with specific reference being made to the drawings in which.

DETAILED DESCRIPTION OF THE INVENTION

Figure 1:
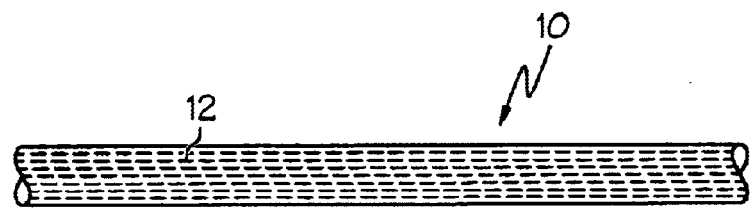
FIG. 1 is a schematic representation of side view of a tubular parison used to produce a balloon of the invention from a the micro-fiber composite material.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

As noted above, the present invention relates to medical catheters which have one or more balloon portions constructed from a specially configured micro-composite material. The particular micro-composite material and configuration provides physical properties which allow a balloon to expand radially to a predetermined extent, but which allow only minimal, or more preferably, no longitudinal growth during expansion. The micro-composite material includes a longitudinal fibril component which exhibits micro-fibers at the molecular level in combination with a matrix of any semi-compliant balloon material. Depending on the specific fibril component, as well as the method of extrusion utilized to extrude the balloon material, the micro-fibers may be randomly scattered through out the balloon material or may be precisely spaced about the balloon and extending through the entire balloon length. The fibril structure is oriented or directed in the longitudinal direction of the balloon providing the balloon with desirable radial expansion characteristics and minimal longitudinal growth when the balloon is inflated.

As shown in FIG. 1, the balloons of the invention may be made from tubular parisons 10 of the micro-composite material, having a fibril component which exhibits micro-fibers 12 uniformly oriented in a predetermined direction. In a preferred embodiment shown in FIG. 2, the micro-composite is formed into a balloon 20 from a parison 10 by a conventional balloon blowing process. Balloon 20 has a diameter D and a length L. Micro-fibers 12 are oriented along and about the longitudinal axis 22 of the balloon at the molecular level. The fibril component may be any rigid-rod or semi-rigid-rod thermoplastic material which comprises 0.1 to about 20 percent, and more preferably from about 0.5 to about 15 percent by weight of the micro-composite material. Examples of suitable materials which could be utilized as the fibril component include: liquid crystal polymers (LCPs), polyetheretherketone (PEEK) material, and PPS. Other materials may also be utilized as the fibril component of the present invention. Such substances include aromatic nylon, rigid polyurethane, polyester, copolyester, polyester blends, polyester/polyurethane blends, PEEK, PPS, fluoropolymer and so on.

The fibril material suitably has melting point of about 275° C. or less, more suitably a melting point of about 250° C. or less, even more suitably in the range of about 150 to about 249° C., and most suitably about 230° C. or less.

In one particular embodiment, the fibril component is LCP and is suitably a thermotropic liquid crystal polymer. Suitably, as noted above, the LCP has a melting point of about 275° C. or less, more suitably about 250° C. or less, even more suitably from about 150 to about 249° C. and most suitably about 230° C. or less. Specific examples of LCPs useful herein include, but are not limited to, VECTRA® LKX 1107, a polyester-type LCP (mp 220° C.), and VECTRA® LKX 1111, a polyesteramide-type LCP (mp 220° C.), both sold by Ticona, a Hoechst company.

The micro-composite material is suitable for use in the compositions herein from about 0.1 to about 20 wt-%, more suitably from about 0.5 to about 15 wt-%, and most suitably from about 0.5 to about 8 wt-%.

A melt compatibilizer, such as disclosed in application Ser. No. 08/926,905, now issued as U.S. Pat. No. 6,242,063, may also be employed in an amount of from 0 to about 30 weight percent.

To form the micro-composite material, the fibril component is preferably combined with a semi-compliant thermoplastic polymer material in a melt blend which at least partially phase separates upon cooling. Under appropriate conditions the phase separated material will form fibrils or micro-fiber 12 embedded in a matrix of the semi-compliant thermoplastic polymer, oriented substantially parallel to the longitudinal axis of the extruded tubing. The micro-composite material suitably employs an amount of semi-compliant polymer matrix component from about 50 to 99.9 percent by weight, preferably from about 85 to 99.5 percent.

Some examples of suitable materials which may be utilized as the matrix component are polyamide-polyester block copolymers, namely the polyamide/polyether/polyesters PEBA® 6333, 7033 and 7233; also polyester-polyether block copolymer such as ARNITEL® 540. Suitably, the matrix component has a melting temperature in the range of about 140° C. to about 265° C.

Suitably, the base polymer or matrix polymer has a melting point within about 70° C., more suitably within about 50° C. and most suitably within about 35° C. of the micro-composite material. Suitably the base polymer has a melting point in the range of from about 140° C. to about 265° C., more suitably about 220° C. or less, and most suitably from about 150° C. to about 210° C.

The polymer may be selected depending on the choice of liquid crystal polymer and what melting temperature it has, for instance. Specific examples of useful base polymers include, for example, but are not limited to, acetal homopolymers or copolymers (typical mp 160–185° C.); cellulosic polymers (mp 140–190° C.); poly(chlorotrifluoroethylene) (mp 200–220° C.); poly(vinylidine fluoride) (mp 155–180° C.); nylon 6,6 (mp 250–260° C.); nylon 6 (mp 215–225° C.); nylon 6,10 (mp 210–220° C.); nylon 12 (mp 170–180° C.); nylon 11 (mp 180–190° C.); polyoxymethylene (mp 165–185° C.); higher melting grades of poly(methyl methacrylate) (e.g. mp 140–160° C.); polypropylene homopolymers and copolymers (mp 160–175° C.); polycarbonate polymers and copolymers (mp 220–230° C.); poly(ethylene-vinyl alcohol) (mp 140–180° C.); polyethylene terephthalate; polybutylene terephthalate; polytrimethylene terephthalate; thermoplastic polyurethanes (aromatic and/or aliphatic); thermoplastic elastomers such as polyester elastomers sold under the tradenames HYTREL® and ARNITEL®; polyamide elastomers sold under the tradename PEBAX®; and thermoplastic polyurethane elastomers sold under the tradename PELLETHANE®. Particularly preferred base polymer materials include PEBAX® 7033 (mp 174° C.) and 7233 (mp 175° C.), sold by Atochem North America, and ARNITEL® EM 740 (mp 221° C.), sold by DSM Engineering Plastics.

In one particular embodiment of the present invention, the micro-composite or fibril component includes an LCP having a melting point of less than about 250° C. and a matrix polymer having a melting temperature in the range of about 140° C. to about 265° C. Use of some of these matrix polymers in LCP blends has been described in the prior application Ser. No. 08/926,905, now issued as U.S. Pat. No. 6,242,063, for instance PET/LCP blends, incorporated by reference herein. However, by using lower melting temperature LCPs, as described herein, processing is made easier. For instance, where there is a large temperature difference between the matrix polymer and the LCP component, a dual extruder may have had to be used to allow the polymers to be separately melted before they could be mixed. With a smaller difference in melt temperatures the melt blend of LCP and matrix polymer can be prepared by melting a dry blend of the two polymers, or one of the two polymers in solid form may be added to a melt of the other, without substantial polymer degradation. A dual extruder technique can still be used to obtain blends with base polymers whose melt temperature is substantially lower than that of the LCP used in the present invention. Therefore the range of usable base polymers is substantially increased in the present invention over those of prior application Ser. No. 08/926,905, now issued as U.S. Pat. No. 6,242,063.

The portion of the device made from the melt blend may be a catheter body segment or a balloon for a catheter. The balloons made from the melt blend of the present invention may be either single layer balloons, or multilayer balloons. As previously described, the present invention achieves the desired balloon expansion characteristics as a result of forming a balloon composed of a micro-composite material. The micro-composite material balloon is formed by coextrusion of a melt blend of LCP or other orientable material, the matrix component, and optionally a compatibilizer. A dual extrusion process utilizing two extruders may also be used to form the desired tube. In the case where LCP is used as the fibril component, the longitudinally oriented fibers are formed by subjecting the blend material to a relatively high extrudate puller speed. The high speed of the puller will subject the blend material to a shearing force which causes a material such as LCP to elongate and form fibers. If the LCP is not subjected to a high shearing force, the LCP will form droplet shaped deposits which provide minimal or no longitudinal stabilization.

If, during extrusion, relative rotation of the mandrel and die is avoided, the fibrils will adopt an orientation substantially parallel to the longitudinal axis. If the die and mandrel are relatively rotated, e/g. by rotation of one or the other or both, the orientation of the fibrils will be helically about the axis.

A balloon which has an LCP fibril component tends to have individual fibers spread randomly throughout the balloon material. The individual LCP fibers will typically be between 0.1 micron to 1 micron in diameter.

If the various components utilized to form the micro-composite material are incompatible to a substantial degree, phase separation may be so efficient that slippage between phases might occur during balloon expansion thereby reducing the longitudinal restriction effect of the fibrils. To prevent such occurrences a compatibilizer may also be desirable for the purpose of enhancing the homogeneity of the melt blend prior to extrusion and cooling. A compatibilizer material may be added to the pre-extruded melt blend material to create a less distinctive phase boundary between the fibril and matrix components. The compatibilizer may be for instance a block copolymer comprising a block which is structurally similar or otherwise is soluble in the matrix polymer and a block which is structurally similar or otherwise soluble with the fibril component. An example of a suitable is the melt compatibilizer disclosed in application Ser. No. 08/926,905 now issued as U.S. Pat. No. 6,242,063.

Such a compatibilizer may be employed in an amount from 0 to about 30 weight percent.

Figure 2:
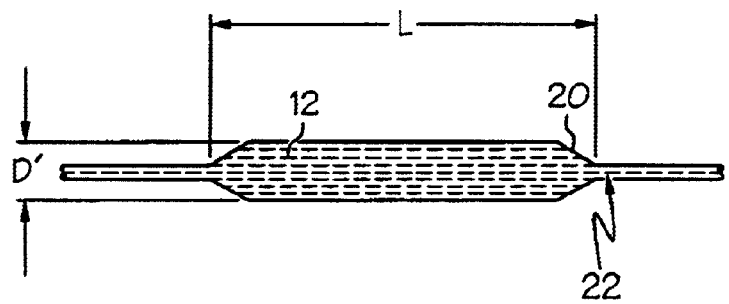
FIG. 2 is a schematic side view of a medical device delivery balloon constructed from micro-composite material shown at nominal diameter wherein the fibril component is oriented parallel to the longitudinal balloon axis.
Figure 3:
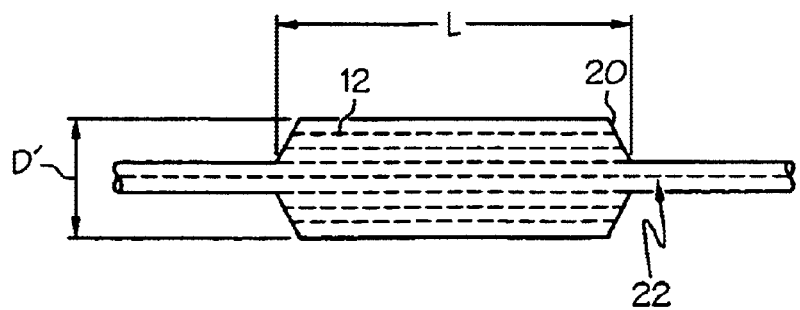
FIG. 3 is a view of the medical device delivery balloon shown in FIG. 2 in an inflated state at a pressure higher which causes radial growth of the balloon.

The balloon 20, shown in FIG. 2 at nominal diameter, is shown in FIG. 3 inflated at a higher pressure which provides radial expansion to a new, larger diameter D'. In the most preferred embodiment, the micro-composite material 10 allows balloon 20 to obtain semi-compliant expansion in the radial direction while negating balloon expansion in the longitudinal direction during inflation (balloon length L is substantially unchanged in FIG. 3). Depending on the precise mixture and type of matrix and fibril components used, other embodiments of the present invention may provide for balloons with varying degrees and types of radial expansion while also reducing longitudinal expansion by varying degrees.

If substances less prone to phase separation from the matrix material are desired to be used, an appropriately shaped die may be used in the extrusion process to provide individually extruded fibers evenly around the tube circumference, for instance in the manner of U.S. Pat. No. 5,389,314 except that the fiber material is selected to adhere to the matrix material and a high line speed is used to provide a microscopic fiber diameter. For such an embodiment, the individual non-LCP fibers will typically be between 10–12 microns in diameter and may also extend through the entire length of the balloon in chain or cores.

Figure 4:
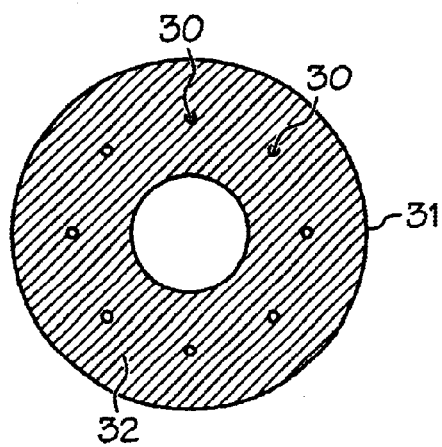
FIG. 4 is a cross-sectional view of a tubular parison for producing balloon of an alternative embodiment of the invention.
Figure 5:
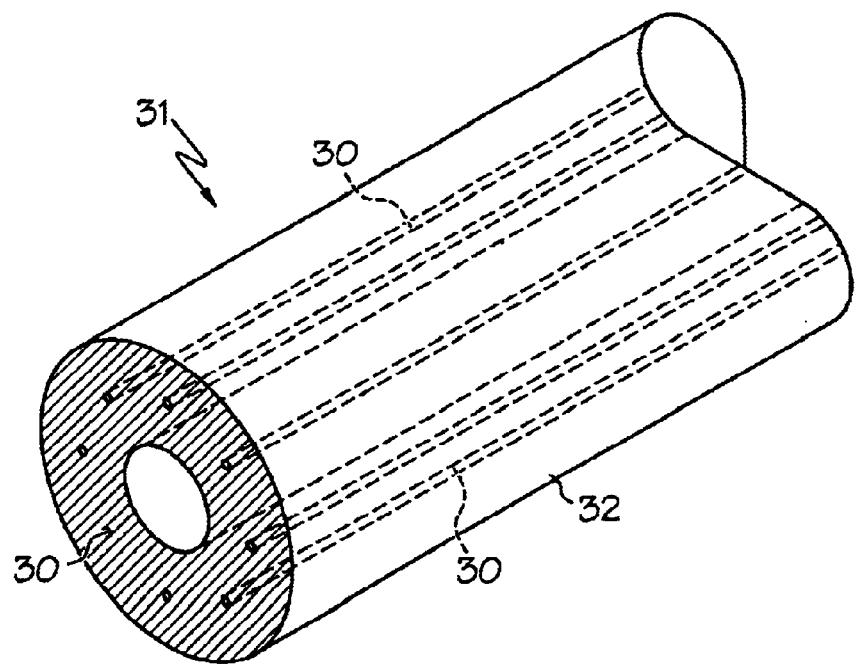
FIG. 5 is a perspective view of the embodiment shown in FIG. 4.

This embodiment is depicted by the tubular parisons in FIGS. 4 and 5. As shown, cores 30 are suspended through out the parison 31 in a matrix 32 which may be composed of any material suitable for constructing a semi-compliant balloon as have been described above. The cores 30 are composed of a material which has a more limited ability to stretch than the matrix material, and when the cores are collectively oriented in the same direction, the structures exhibit an increased longitudinal stability when inflated beyond initial or nominal diameter.

In selecting appropriate materials for the fibrils of cores 30 and matrix 32 it is important to select materials which provide adequate adhesion to one another. If adhesion is insufficient between the cores 30 and the surrounding matrix 32 longitudinal growth of the balloon produced from parison 31 will not be restricted as the more expansive matrix material will slip past the individual cores. A further important attribute of the cores 30 is the bulk elongation of the material when oriented as described above. The bulk elongation of the cores 30 should be within the range of 50%–150%. In order to avoid core breakage prior to balloon bursting, it is desirable to the present invention that if the material from which the cores are constructed exhibit a higher tensile strength than the material of which the matrix is constructed.

Figure 6:
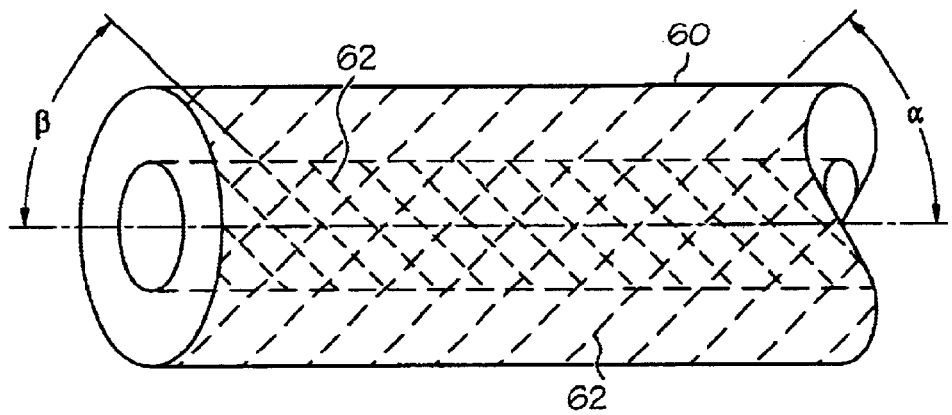
FIG. 6 is perspective view of a dilatation balloon preform in a tubular parison form constructed from micro-composite material wherein the inner and outer fibril components have been oriented diagonally to the longitudinal axis of the tubular preform and in crossing relationship relative to each other by use of a counter-rotating extrusion die.
Figure 7:
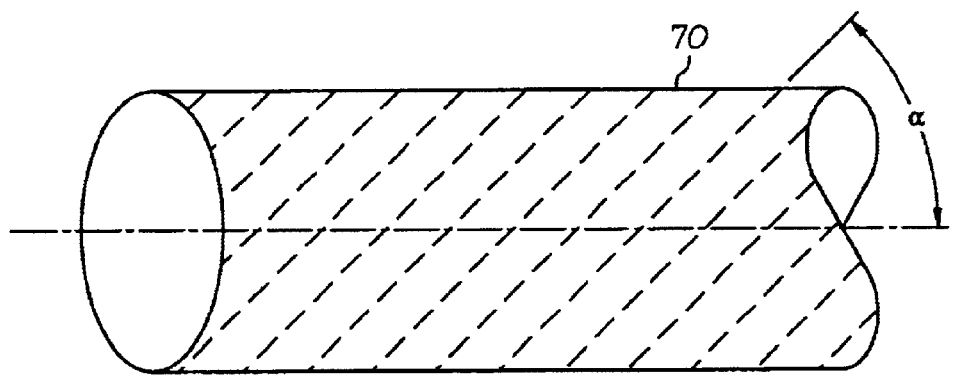
FIG. 7 is another perspective view of only the outer surface of a dilatation balloon preform constructed from micro-composite material wherein the fibril component is oriented diagonally to the longitudinal axis of the tubular preform by use of a rotating die.
Figure 8:
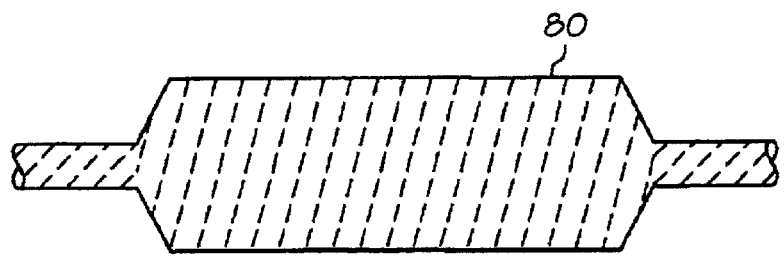
FIG. 8 is a schematic side-view of a blow molded dilatation balloon constructed from micro-composite material depicting the fibril component oriented diagonally to the longitudinal axis of the balloon.

FIGS. 6–8 pertain to alternative embodiments in which the fibers of the balloon are orientated diagonally relative to the longitudinal axis of the balloon. In FIG. 6 there is depicted a parison 60 for a balloon in which, in addition to using a high puller speed during extrusion, a counter rotating die was used. The counter rotating die has a mandrel which rotates in one direction and a concentric outer die which rotates in the opposite direction, the parison is extruded through the space between the two. The resulting parison has fibers 62 orientated diagonally to the parison axis 64 in one direction at the outside surface (angle $\alpha$) and changing gradually as one passes through the material in a direction transverse to the axis 64 to a second direction (angle $\beta$) at the inside surface, the angles determined by outer die/mandrel rotation speeds and puller speed. If one or the other of the outer die or the mandrel are held stationary while the other is rotated, angle α or angle β may be parallel to the axis 64.

In FIG. 7 there is depicted a parison 70, having diagonally oriented fibers formed by relative rotation of the die and puller. For instance only the outer die or mandrel may be rotated so that the fibers become orientated at angle α throughout the entire thickness of the parison.

FIG. 8 depicts the outer surface orientation of a balloon 80 made from a parison of either FIG. 6 or FIG. 7. In the balloon body the fibers retain an angular orientation relative to the balloon axis and provide resistance to both longitudinal and radial expansion beyond the nominal or molded dimensions.

Based on the above description it should be understood that several different polymers with a wide range of characteristics may be used to form a longitudinal or longitudinal and radial stabilized balloon of the present invention. The following is an example of a balloon and its manufacturing parameters which was actually constructed in accordance with the present invention disclosure.

EXAMPLE 1

A matrix component of Pebax 7033 was mixed with a fibril component of LCP VECTRA LKX 1107 at the ratio of 95% to 5% respectively by weight. The mixture was extruded at a rate of 110 feet/minute line speed into tubing of 0.039 (outer diameter) x 0.027 (inner diameter) inch. A 3.5 mm balloon was formed from the resulting tubing by radial expansion at 110 degrees Celsius with blowing pressure of 350 psi. The balloon with double wall thickness of 0.0014 inch was inflated from 4 atm to 13 atm at 1 atm increment and no measurable balloon length change was observed.

This completes the description of the preferred and alternate embodiments of the invention. Those skilled in the art may recognize other equivalents to the specific embodiment described herein which equivalents are intended to be encompassed by the claims attached hereto.

What is claimed is:

1. An inflatable medical balloon which is mounted on a catheter, and has a determined preinflation length, restricted longitudinal and radial characteristics, a circumference and a longitudinal axis, composed of a micro-composite material comprising a polymer matrix component with a polymer fibril component distributed in the polymer matrix component, the polymer fibril component having micro-fibers oriented substantially parallel or diagonally to the longitudinal axis of the balloon, the polymer fibril component composed of one or more members selected from the group consisting of rigid-rod thermoplastic, semi-rigid rod thermoplastic, liquid crystal polymer, which are stronger than the matrix material and have bulk elongation between 50% and 150%, which is less than the matrix material and the fibril component and the matrix component operatively adhere to one another.

2. The inflatable medical balloon of claim 1, wherein said micro-composite material comprises about 0.1 wt-% to about 20 wt-% of said fibril component.

3. The inflatable medical balloon of claim 1, wherein said micro-composite material comprises about 0.5 wt-% to about 8 wt-% of said fibril component.

4. The inflatable medical balloon of claim 1, wherein said micro-composite material comprises about 0.5 wt-% to about 15 wt-% of said fibril component.

5. The inflatable medical balloon of claim 1, wherein said micro-composite material comprises about 50 wt-% to about 99.9 wt-% of said polymer matrix component.

6. The inflatable medical balloon of claim 1, wherein said micro-composite material comprises about 85 wt-% to about 99.5 wt-% of said polymer matrix component.

7. The inflatable medical balloon of claim 1, wherein the micro-composite material further comprises a compatibilizer component.

8. The inflatable medical balloon of claim 7 wherein said compatibilizer is a block copolymer.

9. The inflatable medical balloon of claim 7 wherein said compatibilizer is selected from the group consisting to copolyester elastomers, ethylene unsaturated ester copolymers, copolymers of ethylene and a carboxylic acid or derivative thereof, polyolefins or ethylene-unsaturated ester copolymers grafted with functional monomers, copolymers of ethylene and a carboxylic acid or derivative thereof, terpolymers of ethylene, copolymers of unsaturated esters and carboxylic acids or derivatives thereof, maleic acid grafted styrene/ethylene-butadiene-styrene block copolymers, acrylic elastomers, glycidyl(meth)acrylates, ionomeric copolymers, polyester-polyether block copolymers, and mixtures thereof.

10. The inflatable medical balloon of claim 7, wherein said compatibilizer is selected from the group consisting of ethylene-maleic anhydride copolymers, ethylene-methyl acrylate copolymers, ethylene-methyl acrylate-maleic anhydride terpolymers, ethylene-methyl acrylate-methacrylic acid terpolymers, alkyl(meth)acrylate-ethylene-glycidyl (meth)acrylate terpolymers, and mixtures thereof.

11. The inflatable medical balloon of claim 1, wherein the fibril component has a melting point of about 275° C. or less.

12. The inflatable medical balloon of claim 1, wherein the fibril component has a melting point of about 250° C. or less.

13. The inflatable medical balloon of claim 1, wherein the fibril component has a melting point of about 150° C. to about 249° C.

14. The inflatable medical balloon of claim 1, wherein the fibril component has a melting point of about 230° C. or less.

15. The inflatable medical balloon of claim 1, wherein the matrix component comprises a semi-compliant thermoplastic polymer.

16. The inflatable medical balloon of claim 1, wherein the matrix component has a melting point of about 140° C. to about 265° C.

17. The inflatable medical balloon of claim 1, wherein the matrix component has a melting point of about 150° C. to about 230° C.

18. The inflatable medical balloon of claim 1, wherein the matrix component has a melting point of about 220° C. or less.

19. The inflatable medical balloon of claim 1, wherein the orientation of the micro-fibers relative to the longitudinal axis of the balloon changes through the balloon material in a direction transverse to said longitudinal axis.

* * * * *